(12) United States Patent
Sjoblom et al.

(10) Patent No.: US 6,234,008 B1
(45) Date of Patent: May 22, 2001

(54) METHOD AND APPARATUS FOR THE DIRECT MEASUREMENT OF MOISTURE CHARACTERISTICS OF POROUS SAMPLES OF SOIL, WOOD, CONCRETE AND THE LIKE

(75) Inventors: Kurt Sjoblom, Boston; John T. Germaine, Lexington, both of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/457,176

(22) Filed: Dec. 8, 1999

(51) Int. Cl.$^7$ .............................. G01N 25/56; G01N 5/02
(52) U.S. Cl. ........................................ 73/73; 73/74; 73/76
(58) Field of Search .................................. 73/73, 74, 75, 73/76; 177/25.14

(56) References Cited

U.S. PATENT DOCUMENTS

| | | | |
|---|---|---|---|
| 4,170,251 | * 10/1979 | Hine, II ................................. | 141/11 |
| 4,509,361 | * 4/1985 | Johnson .................................. | 73/73 |
| 4,889,201 | * 12/1989 | Oldendorf et al. ................ | 177/25.14 |

OTHER PUBLICATIONS

David I. Stannard, "Tensiometers–Theory, Construction, and Use," Geotechnical Testing (cont.) Journal, vol. 15, No. 1, pp. 48–58, Mar. 1992.

Yan Guan and D.G. Fredlund, "Use of the tensile strength of water for the direct measurement (cont.) of high soil suction," Canadian Geotechnical Journal, vol. 34, pp. 604–614 (1997).

Kanthasamy K. Muraleetharan and Karen K. Granger, "The Use of Miniature Pore Pressure in Measuring Matric Suction in Unsaturated Soils," Geotechnical Testing Journal, vol. 22, (cont.) No. 3, pp. 226–234, Sep. 1999.

Yanagisawa, K, Ioku, K, and Yamasaki, N, "Pore Size Control of Porous Silica Ceramics by Hydrothermal Hot–Pressing," Journal of the Ceramic Society of Japan, Int. Ed., vol. 102, p. 968 (1994).

Kurt J. Sjoblom and John T. Germaine, poster session entitled "A Direct Measurement Technique of the Soil Moisture Characteristic Curve," presented on Thursday, Dec. 10, 1998, at 1998 Fall Meeting of American Geophysical Union, Dec. 6–10, 1998.

(List continued on next page.)

*Primary Examiner*—Hezron Williams
*Assistant Examiner*—Dennis Loo
(74) *Attorney, Agent, or Firm*—Steven J. Weissburg (57) ABSTRACT

A soil specimen rests on a porous support. The support may be a porous ceramic plate or other body, for instance rated at 15 bar (1,500 kPa) or greater. The plate overlies a reservoir full of water that hydraulically contacts either an elastic membrane, that is fitted with a strain gauge, or a pressure transducer. As the soil specimen dries out, water is drawn from the pore space, which decreases the amount of water surrounding the soil particles, causing an increase in the pore water tension. The tension draws water from the saturated plate and reservoir, causing a change in the output of the strain gauge or pressure transducer. The tension is transduced by the strain gauge or pressure transducer, and is continuously recorded. The entire apparatus described above may rest on a balance. As the soil dries out, and its mass is reduced, the change in mass can be measured, and from the change, the mass of the remaining soil and water can be determined. From this, the soil moisture content over time can be calculated. The mass and the tension are recorded, essentially continuously during this process. A continuous relationship between soil water content and soil pore water tension is then calculated and plotted, as a Soil Moisture Characteristic (SMC). A complete curve over all moisture contents and soil tensions can typically be completed within twenty-four hours using the present invention.

43 Claims, 8 Drawing Sheets

OTHER PUBLICATIONS

Ridley, A. M., and Wray, W. K., "Suction measurement: A review of current theory and practices," Unsaturated Soils (Alonso & Delage (eds.)) pp. 1293–1322, AA Blakema, in $1^{st}$ International Conference on Unsaturated Soils, Paris, France (1996).

Soilmoisture Equipment Corp., Santa Barbara, CA, Porous Ceramics 600 Series brochure, Mar. 1996.

Soilmoisture Equipment Corp., Santa Barbara, CA, brochure regarding ceramic plates and membranes.

American Standards for Testing and Materials, "Standard Test Method for Capillary–Moisture (cont.) Relationships for Fine–Textured Soils by Pressure–Membrane Apparatus," by Porous–Plate Apparatus, ASTM D2325–68 (Reapproved 1981).

American Standards for Testing and Materials, "Standard Test Method for Capillary–Moisture (cont.) Relationships for Fine–Textured Soils by Pressure–Membrane Apparatus," ASTM D3152–72 (Reapproved 1977).

* cited by examiner

METHOD AND APPARATUS FOR THE DIRECT MEASUREMENT OF MOISTURE CHARACTERISTICS OF POROUS SAMPLES OF SOIL, WOOD, CONCRETE AND THE LIKE

BACKGROUND

This invention relates generally to moisture characteristics of porous materials, such as soil, wood, concrete and the like. It relates more particularly to a method and apparatus for directly measuring the moisture characteristic curve of such a porous material by measuring the pore water tension within the body, while simultaneously recording the change in mass due to removal of water.

Figure 1A:
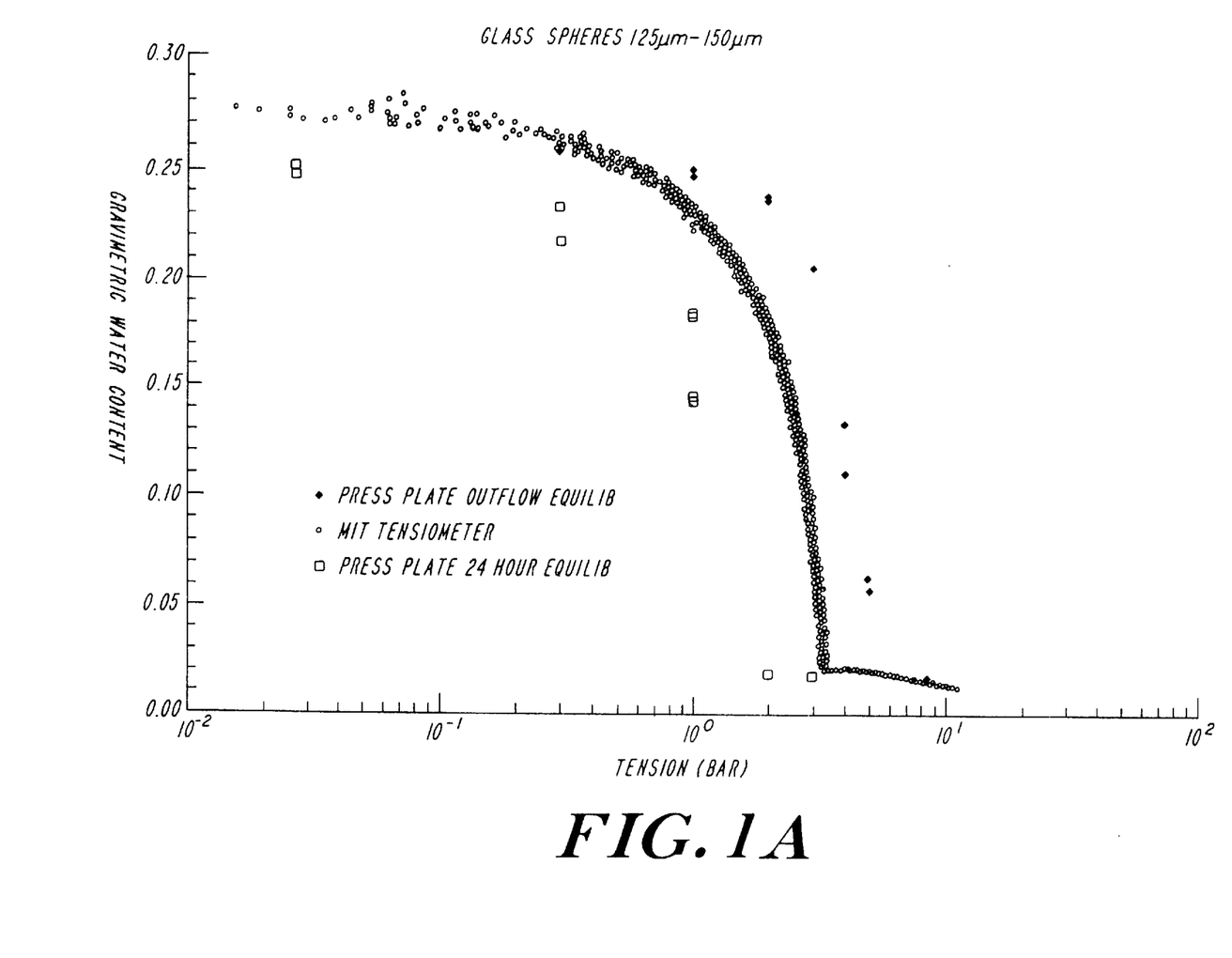
FIG. 1A is a graph, showing the relationship between moisture content and tension, for glass spheres.
Figure 1B:
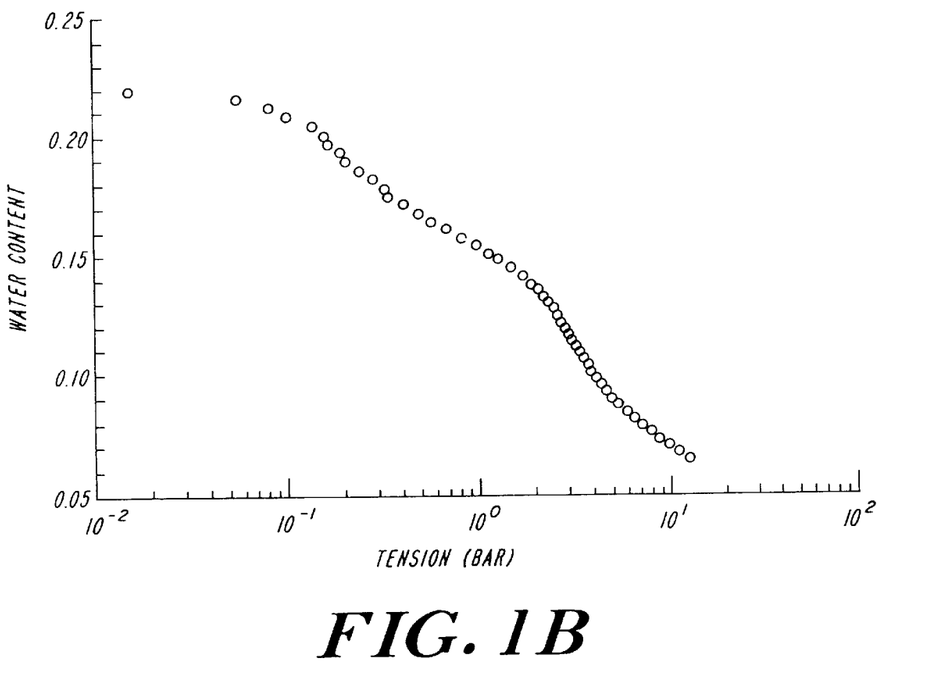
FIG. 1B is a graph, showing the relationship between soil moisture content and tension, for a typical silty soil.

The behavior of extended porous bodies, such as soil, and more discrete porous bodies, such as lumber and concrete, can be understood and anticipated, to some extent, with knowledge of the bodies' moisture characteristic. The moisture characteristic relates, on the one hand, moisture content, and, on the other hand, induced liquid tension. For instance, it is common to represent the moisture characteristic of soil as a curve, relating soil water content by mass to soil water tension, measured in bars, or kPa. In the field of soil mechanics, the characteristic is called the Soil Moisture Characteristic ("SMC"). For purposes of generality, the characteristic will be referred to herein as simply the Moisture Characteristic ("MC"), indicative of the fact that porous bodies other than soil may also be analyzed with reference to their moisture characteristics. FIG. 1A shows a typical MC for a sample of glass spheres, rather than soil. The regular curve, identified by small circles, was generated using an embodiment of the invention, discussed below. The data points indicated by open squares were generated using a prior art pressure plate apparatus, after the specimen is maintained under a pressure for 24 hours. The data points indicated by solid diamonds were generated using a prior art pressure plate apparatus after observable outflow terminated.

FIG. 1B shows an SMC for a specimen of soil, generated using an embodiment of the invention, discussed below, having a curve that has several changes in slope and curvature resulting from the more complicated pore structure of the soil as compared to that of the glass beads.

Rather than "tension," this property of soil is sometimes referred to as "suction." The term "suction" is used in various ways in the literature. For a good review of these variations, see, Ridley, A. M., and Wray, W. K., "Suction measurement: A review of current theory and practices, Unsaturated Soils (Alonso & Delage (eds.)) pp. 1293–1322, AA Blakema, in $1^{st}$ International Conference on Unsaturated Soils, Paris, France (1996), which is incorporated fully herein by reference.

As used herein, "suction" or "tension" refers to the "matric" suction, which is a measure of the energy resisting movement of a molecule of water into the soil matrix from a reference pool, under isothermal condition and at constant elevation and pressure.

Knowledge about the SMC is useful to agronomists for many tasks. It can aid determination of suitability for various types of plant growth, and when or how frequently to water. It may also be used to determine how contaminants in ground water, or soil will be transported throughout the soil, and to analyze the behavior of contaminant plumes.

Insight regarding the strength of soils may also be gained using the SMC.

Meteorologists may also use knowledge of the SMC to enable them to determine the heat transfer properties across the landscape, which influences weather patterns.

Foresters may also use the SMC to determine whether a forest is at risk for irreversible fire damage, as opposed to whether such a forest might receive benefits from periodic burning, to a certain degree.

Civil engineers may use the MC of concrete to assess its integrity. It is thought that water tension in concrete is related to the propensity to experience micro cracks, which are the progenitors of macro cracks and subsequent failures.

The presently used methods for establishing SMC are inadequate for several reasons. One method is according to an ASTM standard, and uses a porous pressure plate. The porous plate method is used to determine the moisture—suction relationship for coarse and medium grained soils. The technique is recommended for suctions between 0.1 and 1 ATM. The use of this method is outlined in ASTM D2325-68 and is shown schematically with reference to FIG. 2. A similar method for higher suctions (finer textured soils) is set forth at ASTM D3152, recommended for suction up to 15 ATM.

Figure 2:
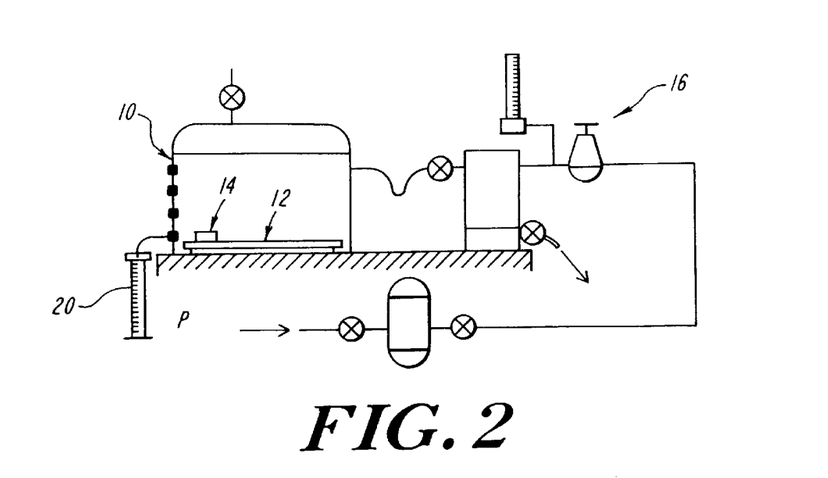
FIG. 2 is a schematic representation of an apparatus of the prior art used to determine SMC, according to ASTM D2325-68.

The ASTM method uses a pressure container 10, a fine pore porous ceramic plate 12, brass screen, rubber (neoprene) membrane, sample rings, and various tubing and spouts. Approximately twenty-five grams of soil 14 is placed into a retainer ring ten mm high by fifty mm in diameter. The specimen and saturated porous plate 12 are then placed into the pressure chamber 10, where the air pressure is regulated by an outside source 16. By raising the air pressure in the chamber 10 to the desired value, drainage of the soil pore water is initiated and the expelled water is removed into a graduated cylinder 20 from the system via an underlying brass screen and neoprene membrane. The chamber pressure is maintained until cessation of pore water flow into the graduated cylinder. At this point, the chamber pressure is released and a water content of the sample 14 is taken by measuring the mass, first wet, and then oven dried.

Since the pore water is free to drain to an outside sink that is open to the atmosphere, the difference in chamber pressure to atmospheric pressure is assumed to be equal to the matric suction. A major drawback of this prior art technique is that it takes several weeks, or even months to generate an SMC curve. This is because each measurement establishes only a single data point relating water content to imposed pressure. Further, it can take several days to collect each data point, because it takes a long time for the plate to saturate, and after that, a long time to come to equilibrium (i.e., for the water to cease flowing out of the chamber into the graduated cylinder 20).

Thus, for each point of tension, a new run of the experiment must be conducted. Typically, only a few data points (fewer than ten) can be generated during practical time periods. The ASTM technique has many additional drawbacks, in addition to the lengthy time. One relates to a certain level of detail in the true SMC curve. Typically, the true SMC curves have a variable fine scale shape as shown in FIG. 1B, which occurs at a scale that is too fine to be captured by the small number of data points sampled with the prior art method. What is needed is a substantially continuous test.

Further, each test (i.e., each pressure) is run on a different specimen of soil. Thus, if sample storage, or collection is not adequately controlled, different data points will actually refer to different soil conditions.

It is difficult to determine when the system has come to equilibrium (i.e., when the water has ceased to flow into the cylinder), and thus from one specimen to the next, there is no certainty that similar situations are being compared, especially if different operators have conducted the tests. One reason for this is believed to be, that while the air pressure is applied to the soil, the soil specimen becomes drier even if no additional fluid collects in the graduated cylinder. Thus, more than one mechanism would seem to be at play in the soil moisture reduction.

Further, when the pressure is relieved and the specimen is removed from the pressure chamber, water that is in the apparatus (membrane, tubing, etc.), returns to the specimen due to the momentary pressure differential. Thus, the subsequent wet mass measurement of the soil does not actually correspond to the imposed pressure. This problem is mentioned in the ASTM documentation. This may be thought of as an elastic rebound of the system.

Another drawback is that the prior art method does not directly measure tension. It imposes a positive pressure and makes an inference that the moisture content under tension would be the same.

Thus, regarding soil, and SMC, there is a significant need for a method and apparatus to measure SMC that can provide results within a few hours. Further, there is a need for a system that can generate an SMC that is continuous over a wide range of soil moisture contents and liquid tensions and that is sensitive to fine scale detail of such characteristics. There is also a great need for a system that provides reproducible results, and that performs all relevant tests on the same specimen, rather than upon different specimens that must be carefully processed to minimize specimen geometry differences. There is also a need for a method and apparatus that directly measures the tension in the pore liquid, and that does not experience elastic rebound.

Thus, the several objects of the invention include to enable generating moisture characteristics, particularly for soil, within a practically short period of time, on the order of hours or a few days, rather than weeks. Another object is to enable such MC generation reproducibly, without regard to specimen size, geometry or ambient humidity, and to enable generation of an entire MC curve, over various moisture contents and tensions, using the same specimen. Another object of the invention is to generate such MC curves substantially continuously over both moisture content and tension ranges, with a level of detail that is much finer than is now available. It is a further object to provide a system that measures pore tension directly.

SUMMARY

In general, using a water bearing soil sample as an example, according to the method of the present invention, a soil specimen is placed on a base capable of directly measuring soil pore water tensions. The soil is allowed to dry out by evaporation, thus increasing the tension in the pore water. The mass and the tension are recorded, essentially continuously during this process. A continuous relationship between soil water content and soil pore water tension is then calculated and plotted, as a Soil Moisture Characteristic (SMC).

According to a preferred embodiment of the apparatus of the invention, the base may be a porous ceramic plate, for instance rated at 15 bar (1,500 kPa) or greater (with the apparatus being limited practically to measuring tensions at less than the plate rating). The plate overlies a reservoir full of water that hydraulically contacts either an elastic membrane, that is fitted with a strain gauge, or a pressure transducer. The entire apparatus described above may rest on a balance. As the soil dries out, and its mass is reduced, the change in mass can be measured, and from the change, the mass of the remaining soil and water can be determined. From this, the soil moisture content over time can be calculated.

As the soil specimen dries out, water is drawn from the pore space, which decreases the amount of water surrounding the soil particles, causing an increase in the pore water tension. The tension draws water from the saturated plate and reservoir, causing a change in the output of the strain gauge or pressure transducer. The tension is transduced by the strain gauge or pressure transducer, and is continuously recorded. This tension is then related to the calculated moisture content at corresponding times, from which the SMC curve is generated.

Rather than setting the entire apparatus on a balance, a force sensor, or other appropriate transducer can be built into the stand upon which the specimen rests, and from the change in gravitational force applied, the change in mass can be determined. A complete curve over all moisture contents and soil tensions can typically be completed within twenty-four hours using the present invention.

Thus, a preferred embodiment of the invention is a method for generating a signal that corresponds to a moisture content characteristic, which characteristic relates tension in liquid residing within a specimen of a porous material, to liquid content of the specimen. An apparatus is provided that comprises a porous body having a specimen surface and a reservoir surface, the reservoir surface facing and in hydraulic contact with a reservoir. Also part of the apparatus is a first transducer, coupled to the reservoir and arranged upon activation to generate a signal that corresponds to tension within the reservoir. The apparatus also includes, supporting the porous body, a second transducer, arranged upon activation to generate a signal that corresponds to the mass of the specimen. The method further comprises the steps of: saturating the pores of the porous body and filling the reservoir with the liquid; placing the specimen upon the specimen surface of the porous body, in hydraulic contact with the porous body; and monitoring a signal from the first transducer, and correlating the signal to tension within the reservoir. While conducting the step of monitoring the signal from the first transducer, the method further comprises step of causing the liquid to exit the specimen. While conducting the steps of monitoring the signal from the first transducer, and causing liquid to exit the specimen, the method further comprises conducting the steps of: monitoring a signal from the second transducer; and correlating the signal from the second transducer to liquid content of the specimen, to arrive at the moisture content characteristic.

According to another preferred embodiment of the method of the invention, the step of correlating the signal from the second transducer comprises the steps of: removing the specimen from the body; measuring the mass of the specimen; drying the specimen, to remove substantially all of the liquid; and measuring the mass of the dried specimen.

The method of the invention may further comprise the steps of periodically recording the signals from the first and second transducers (tension and mass) and correlating the signals with the time at which they were recorded. The correlation may be applied to a plurality of signals, taken at a plurality of times, and may be done graphically, tabularly, or by other suitable means.

The method of the invention may further comprise the step of using a desiccant to promote the exit of liquid from the specimen, or, alternatively, using a vacuum or heat.

According to yet another embodiment of the method of the invention, the step of saturating the porous body comprises the steps of simultaneously applying liquid under pressure to the specimen surface of the porous body and liquid or gas under opposite and substantially equal magnitude pressure to the elastic wall, opposite the reservoir. Prior to the saturation step, a vacuum can be applied to the porous body to remove air.

Still another embodiment of the method of the invention comprises the step of calibrating the first transducer by: applying a plurality of known, positive pressures to the elastic wall, opposite the reservoir; collecting a signal output from the first transducer corresponding to each of the plurality of positive pressures; and recording the signals against the known positive pressures, thereby calibrating the first transducer.

The method of the invention may be applied to soil, wood, concrete, and other liquid containing porous materials.

According to another aspect of the invention, the invention is an apparatus for generating a signal that corresponds to a moisture content characteristic, which characteristic relates tension in liquid residing within pores of a specimen of a porous material, to liquid content of the specimen. The apparatus comprises: a porous body, having a specimen surface and a reservoir surface; a reservoir, adjacent the reservoir surface of the porous body, the porous body arranged with the reservoir surface in hydraulic communication with the reservoir; a first transducer, coupled to the reservoir and arranged, upon activation, to generate a signal that corresponds to tension within the reservoir; and supporting the porous body, a second transducer, arranged, upon activation, to generate a signal that corresponds to mass of the specimen.

The first transducer may be a pressure transducer having a pressure sensitive member that is in hydraulic communication with the reservoir. It may be a strain gauge that is coupled to an elastic wall of the reservoir, to generate a signal that corresponds to strain of the wall. The first transducer may also be one of a number of displacement transducers, including proximity transducers, hall effect transducers, etc. The second transducer may be a balance or a force transducer.

In another preferred embodiment of the invention, the reservoir and the porous body are rigidly sealed from the surrounding environment, except at the specimen surface of the porous body.

According to yet another preferred embodiment of the apparatus of the invention, it comprises means for correlating the signals that corresponds to tension and mass to a time at which the signals were generated, and signals that were generated at identical times to each other, continuously over time. This may include means for graphing or tabulating the signals of tension and mass against each other.

Still another preferred embodiment of the apparatus of the invention comprises the porous body as a ceramic body, comprising a pore diameter of between 50 and 30 nm, with a pore volume of between 0.1 and 0.8 cm$^3$/g. The body may be ceramic, or other material. It may be plate shaped, or not.

A preferred embodiment of the apparatus of the invention may also comprise a second, pressurizeable chamber that includes as a wall, the obverse face of an elastic wall of the reservoir. The apparatus of the invention may also comprise means for providing liquid at a positive pressure relative to atmospheric to the porous body, and thereby to the reservoir face of the elastic wall. Still another embodiment of the apparatus further comprises means for providing fluid or gas at a positive pressure relative to atmospheric to the second, pressurizeable chamber.

According to yet another preferred embodiment of the invention, the first, tension transducer may comprise a differential pressure transducer.

BRIEF DESCRIPTION OF THE DRAWINGS

These and other features, aspects, and advantages of the present invention will become better understood with regard to the following description, appended claims and accompanying drawings, where:

DETAILED DESCRIPTION

In the discussion that follows, a generic embodiment of the apparatus using a generic transducer is first outlined, followed by a description of an embodiment that uses a strain gauge. Next, the basic method of the invention is discussed. This is followed by a discussion of the theory underlining the invention. Set-up procedures (calibration and saturation) follow, followed in turn by a discussion of variations in transducers and porous bodies.

Figure 3:
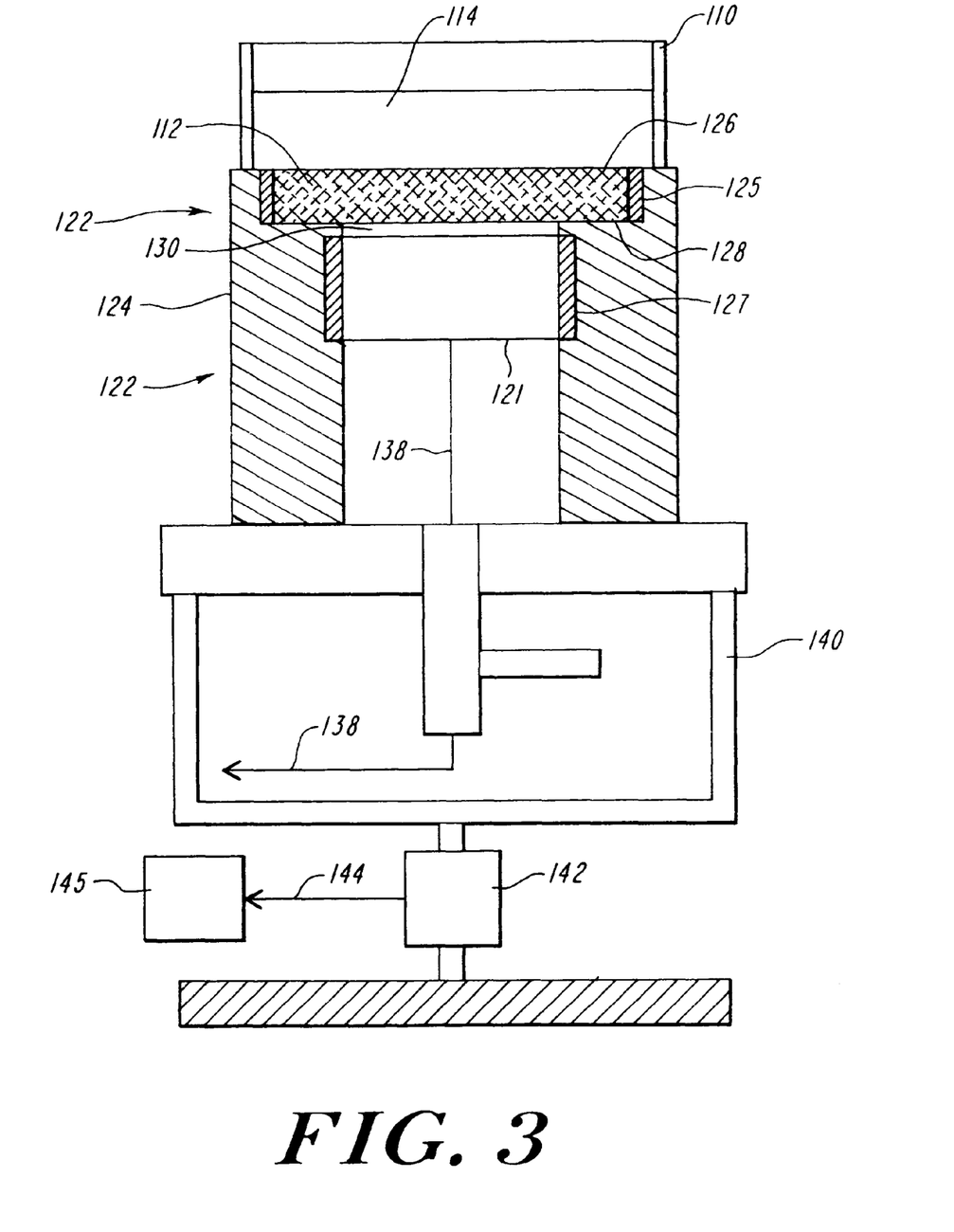
FIG. 3 is a schematic representation of an embodiment of the apparatus of the invention, showing a generic tensiometer.
Figure 4:
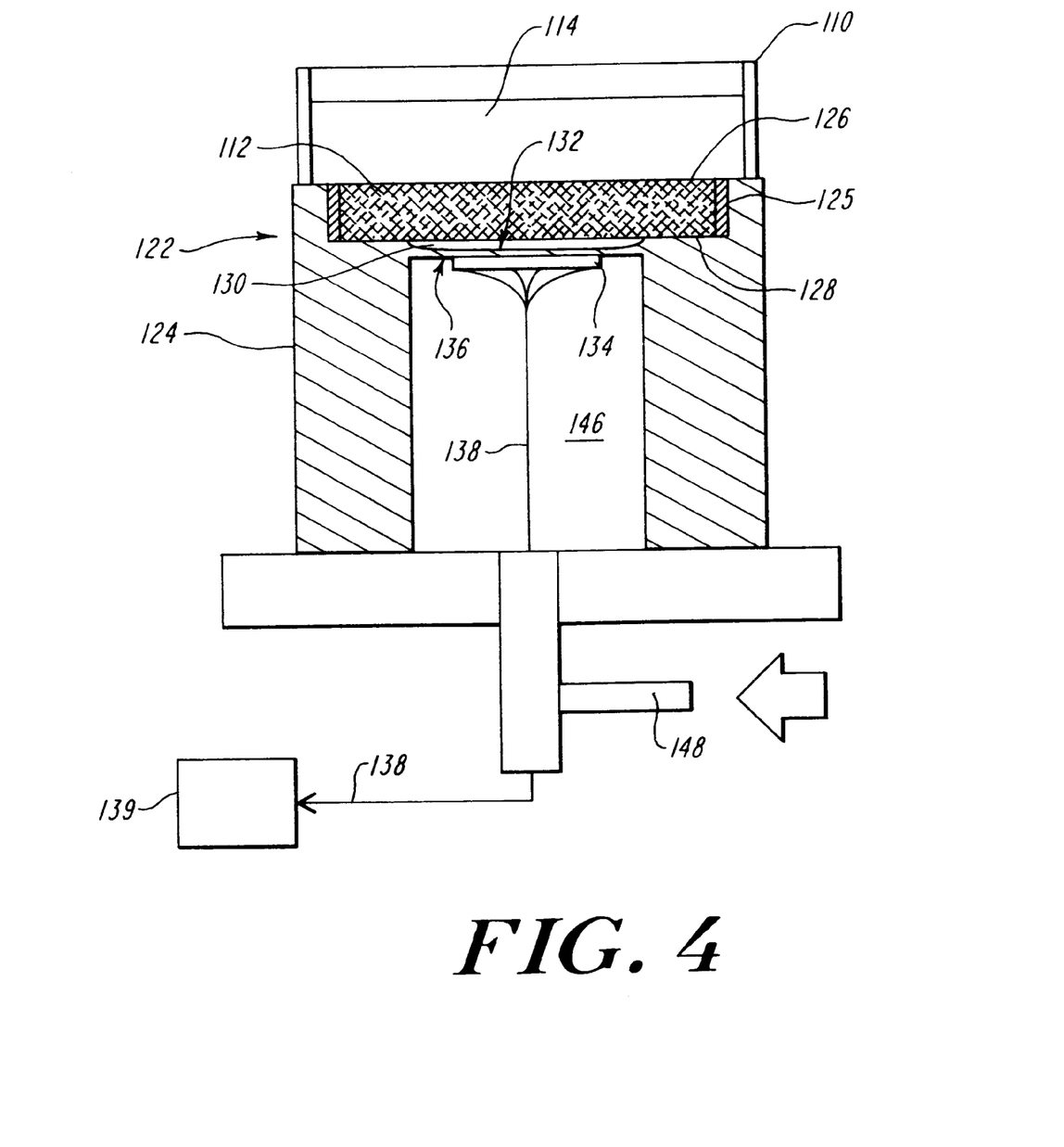
FIG. 4 is a schematic representation of an embodiment of the apparatus of the invention, showing a strain gauge, tensiometer, omitting for simplicity elements that measure mass.

A preferred general embodiment of the apparatus of the invention is shown schematically with reference to FIGS. 3 and 4.

Basic Apparatus

A retaining ring 110 rests on a rigid support 124, described in more detail below. The ring 110 is not sealed or pressurized, and is open to the surrounding atmosphere, which is typically temperature controlled, although, it need not be. The ring is normally at atmospheric condition throughout the test. A soil specimen 114 is inside the ring, in contact with a porous body 112, in the case shown, a plate. The porous plate 112 interfaces with a tensiometer 122.

The tensiometer 122, in one embodiment, includes the rigid support 124, into or upon which is rigidly sealed the porous plate 112, by a rigid seal 125. (The importance of the rigidity of the seal is discussed below.) The porous plate 112 has a soil specimen face 126 and an obverse reservoir face 128. The obverse reservoir face 128 abuts, over part of its surface, on the order of 50%, a reservoir 130, formed in the support 124, or otherwise suitably fabricated. A transducer 121 is rigidly sealed to the support 124 by a rigid seal 127, and is coupled to the reservoir 130 to transmit tension therebetween. The transducer 121 generates a signal over line 138 that corresponds to liquid tension in the reservoir 130. Various types of transducers can be used.

Figure 6:
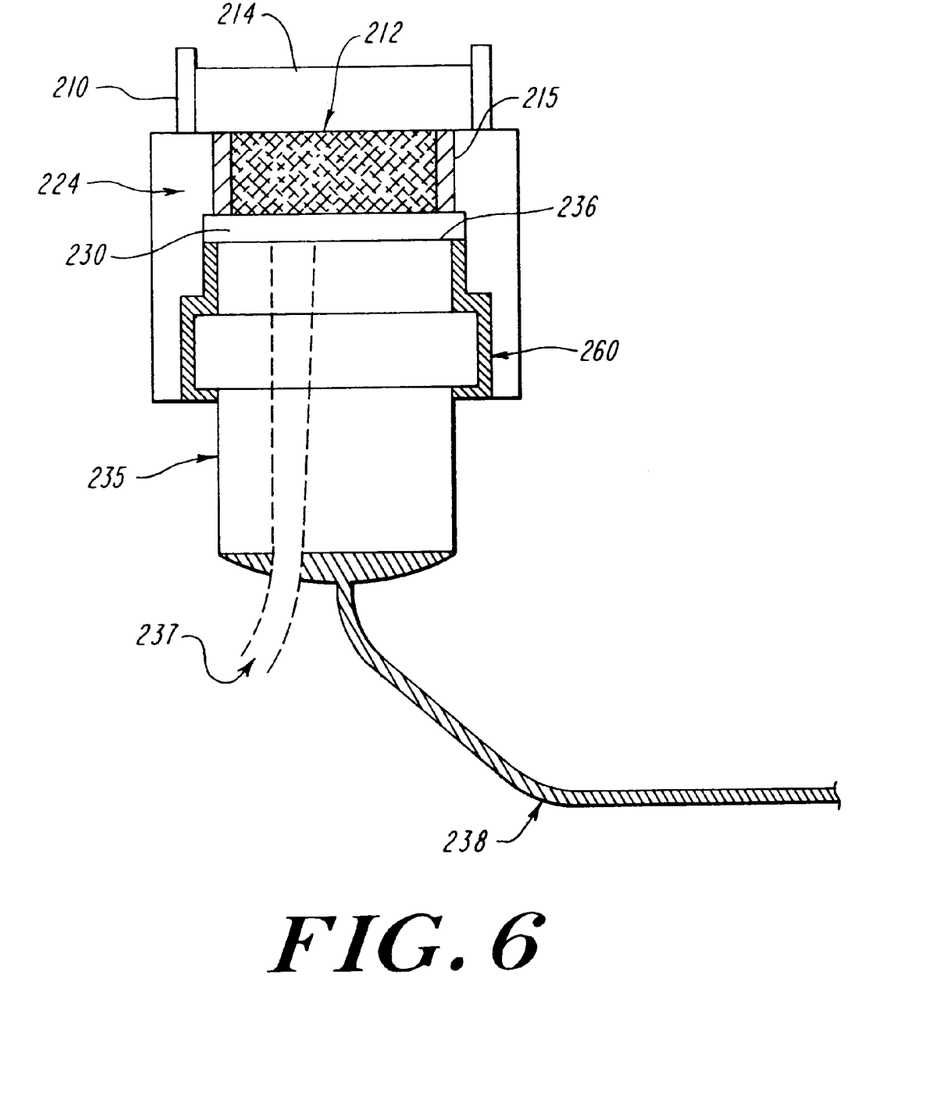
FIG. 6 is a schematic representation of another preferred embodiment of the apparatus of the invention, where, rather than a strain gauge mounted on an elastic wall, a pressure transducer is used in the tensiometer.

For an embodiment shown in FIG. 4, the reservoir has a wall, typically the bottom wall 132, which is elastic and flexible to a degree that it will strain under tensions (negative pressures) applied by suction in the soil specimen 114. The transducer 121 is a strain gauge 134, which is bonded on the face 136 of the elastic wall 132 that is opposite the reservoir 130. (In other embodiments, for instance as shown in FIG. 6, discussed below, the function of the elastic wall is performed by a component of the transducer 121.) Signals from the strain gauge 134 are output over line 138 to suitable data acquisition and management equipment 139, such as a properly programmed general purpose digital computer, or dedicated, specialized hardware and software. Many variations are possible, including custom integrated circuits.

As is discussed below, in more detail, the fluid in the reservoir 130 is in a stress state where the pressure is less than that of atmospheric. This may be referred to herein as "negative pressure," or "tension."

Returning to FIG. 3, the tensiometer 122 and the retaining ring 110 to which it is connected, are both supported by a frame 140, which is itself supported by a force transducer 142, such as a balance, or a specialized transducer. A data output line 144 from the force transducer 142 carries signals that correspond to the mass of the apparatus to suitable data acquisition and management equipment 145, such as a properly programmed general purpose digital computer, or dedicated equipment, as discussed above. Typically, the data acquisition and management equipment 139 for the tension and 145, for the mass are coupled, and would typically be part of the same apparatus. (For simplicity, the elements just discussed that are used to measure mass are not shown in FIG. 4. However in an actual apparatus, they would be present.

Basic Method

The basic apparatus is used as follows. The steps of the method of the invention may also be understood with reference to FIG. 9, which is a flow chart. For simplicity, some steps are not discussed during the initial description of the method, but are discussed further below, after the basic method is described. It will be assumed that the transducer 121 has been calibrated 302. Calibration is discussed below.

Figure 9:
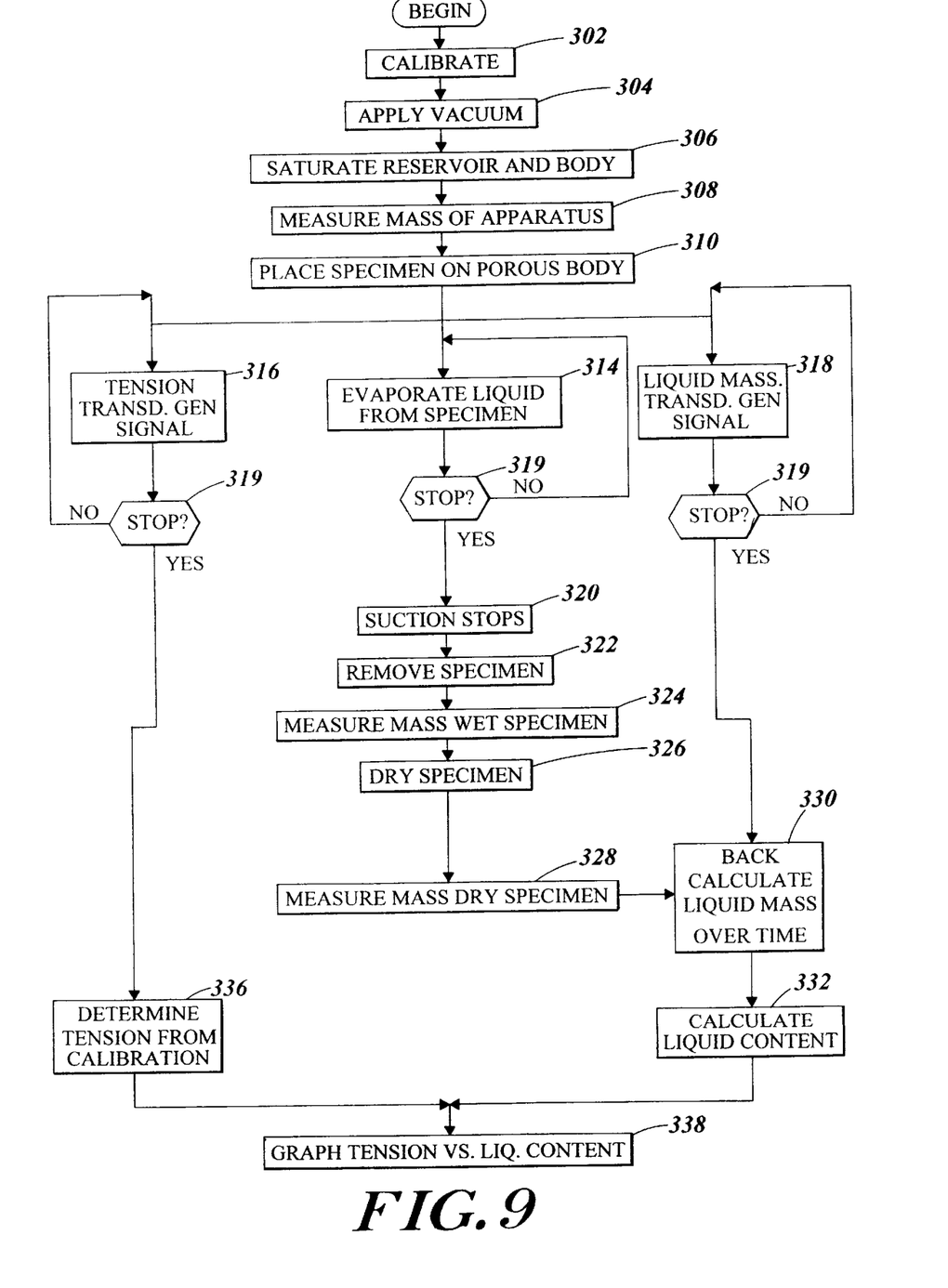
FIG. 9 is a schematic representation, in flow chart form, of an embodiment of the method of the invention.

The porous plate 112 and reservoir 130 are saturated 306 with water. Saturation removes air bubbles. Air bubbles present sites for cavitation, which breaks or limits the suction, thereby letting the tension reduce to whatever is ambient surrounding the fluid.

The procedure for saturating 306 the plate 112 and reservoir 130 is explained in more detail below. However, in general, liquid must be forced through the plate at a pressure higher than the absolute value of the tension it is expected to measure. For instance, it has been found that one type of ceramic plate, available from Soil Moisture Equipment Corporation, Santa Barbara Calif., under model number 1500 rated at 15 bar, must be subjected to 40–45 bar, to subsequently sustain a tension of 15 bar. Another type of ceramic plate requires only 22 bar to subsequently sustain a tension of 18 bar. This second type of plate is described in Yanagisawa, K, Ioku, K, and Yamasaki, N, "Pore Size Control of Porous Silica Ceramics by Hydrothermal Hot-Pressing," Journal of the Ceramic Society of Japan, Int. Ed., Vol. 102 p. 968 (1994) which is incorporated herein fully by reference. The present inventors have used a plate that corresponds to that defined, in part, by curve b, of FIG. 12, showing a pore diameter of between 20 or 30 and 50 nm, for a cumulative pore volume of between 0.1 and 0.8 cm$^3$/g. This plate was prepared according to the techniques of the paper using 9.1% water content, 20 MPa pressure for 1 hour at 300° C. The present inventors have obtained plates from the above mentioned authors and have used them satisfactorily.

In general, "saturation" is a question of degree. Before applying the saturating liquid, a vacuum 304 is applied. Air is drawn out of the plate. A saturation pressure 306 is applied and compresses any remaining air bubbles into smaller and smaller pore crevices. The degree of "saturation" achievable is a measure of the plate's tensile capacity.

After the plate 112 and reservoir 130 have been saturated 306, a mass measurement of the unloaded apparatus is taken 308, and then, a specimen 114 of water bearing soil is placed 310 upon the porous body. Because the pore water in the soil is in hydraulic communication with the surface of the saturated porous plate, which itself is in hydraulic communication with the water in the reservoir, it is believed that the tension (negative pressure) throughout the pore water in the soil, the water in the porous plate, and in the reservoir, is equal, or substantially equal.

The soil specimen 114 is exposed to an atmosphere that will promote evaporation 314 of the liquid from the soil surface. As the liquid evaporates 314, the volume of pore water in the soil specimen 114 reduces, which results in increased tension in the pore water remaining in the soil. The increased tension in the pore water in the soil is felt in the water in the porous plate 112 and the reservoir 130, and thus results in additional strain of the elastic wall 132. This strain is sensed by the strain gauge 134, which generates 316 a corresponding signal that is read on line 138 by data acquisition equipment 139.

Typically, a desiccant is provided in the surrounding atmosphere to help with the drying process. However, other methods (heat, partial vacuum, etc.) may be used to promote, accelerate or actively control the rate of moisture loss from the specimen surface. The rate of moisture loss must be slow enough to allow the water tension to equilibrate throughout the specimen, porous plate and reservoir. In addition, the method used to cause moisture loss must not influence or cause errors in the measurements of tension or specimen mass. For instance, if heat is to be used, the components of the apparatus must be designed such that differential thermal strains do not produce error in the tension signal.

In general, the tension increases because as the soil water evaporates, the remaining water in the soil attempts to minimize its surface area in the soil, pulling water capillarily from the saturated plate 112 and filled reservoir 130. Basically, the porous plate serves to support the soil, while simultaneously providing a pressure transmitting path between the pore water and the thin elastic wall 132. Thus, porous bodies other than a ceramic plate may be used, as long as they can support the specimen, and can provide appropriate porosity for transmission of the fluid tension. The body need not be ceramic, and it need not be plate shaped. What is required is that its pores be small enough to maintain the tension desired to be measured.

Simultaneously with the evaporation 314 and changes in tension, the mass of the items that are supported by the force sensor 142 or balance is being reduced, because pore water is leaving the soil and going into the atmosphere. The mass of the water and soil is continuously measured 318 by the force sensor or balance. The mass of the water that has evaporated is not measured.

The process of simultaneous evaporation 314, tension increase measurement 316 and mass decrease and measurement 318, continues as indicated by the loops in the flow chart around each step. The flow chart indicates a decision 319 as to whether to continue measuring evaporation, measurement of tension and measurement of mass. Typically, the tension measurement stops 320 when the tension is broken, usually due to cavitation. This typically occurs at around 15–20 ATM of tension, with the above-referenced porous plate from the Japanese paper. It would be desirable to measure higher tensions, and, if suitable porous bodies are available, then tension can be measured until cavitation or some other failure occurs. The tension is determined 336 based on the displacement transducer signal, in conjunction with calibration of the transducer.

The water content (by mass) of the soil over time is determined as follows. At the end of the tension measurements, the soil specimen is removed 322 from the porous plate and a measurement is taken 324 of the mass of the soil specimen that was tested. This mass is made up of soil and pore water at the end of the test. The specimen is then oven dried 326 so that all of the remaining pore water is removed. An oven dry mass measurement is then taken 328. The difference between the wet and dry masses is the mass of pore water at the end of the test.

Since a constant record of wet specimen mass was taken 318 during the test, there is a record of the mass of water lost during the test. By backcalculating 330, the water mass throughout the test can be determined. The dry soil mass (which is constant throughout the test) is also now known from dry mass measurement step 328. From measured mass, relative mass is calculated 332 of both water and soil. If relative weight or volume is desired, either can be calculated.

The SMC curve is graphed 338 by coordinating tension and liquid content data, determined to correspond to identical times. By comparing these data for identical times over the entire duration of the evaporation, a continuous curve such as shown in FIG. 1B is generated.

Figure 7:
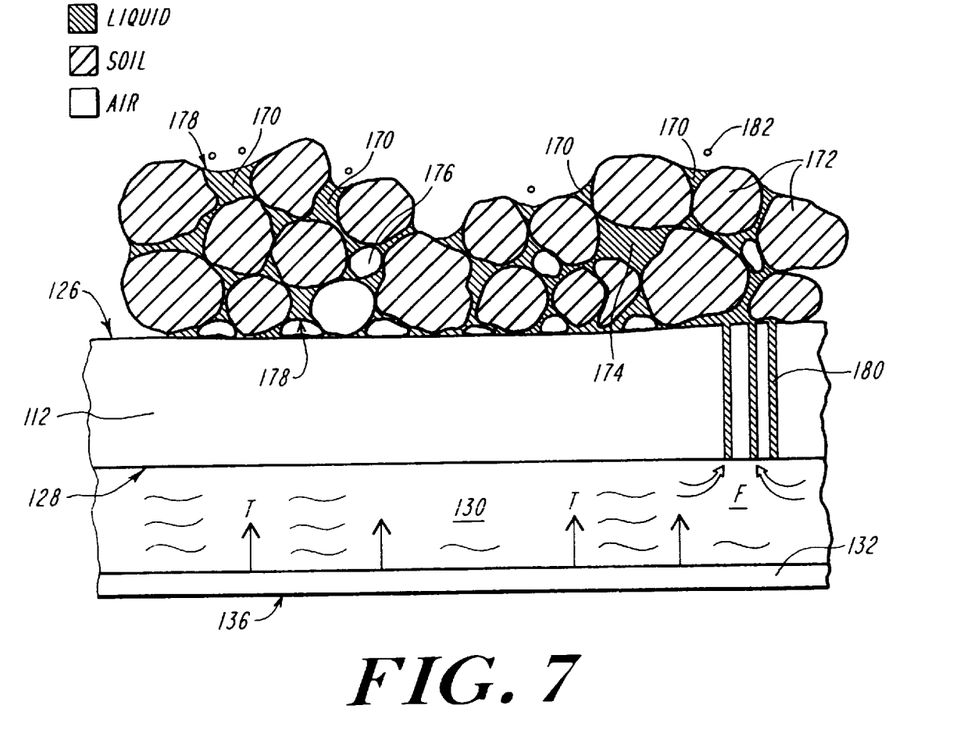
FIG. 7 is a schematic representation of a water-bearing soil specimen.

Reference to FIG. 7 aids understanding of the phenomena under examination. The goal is to measure the relationship between the soil pore water tension and the water content of the soil. The pore water tension is a measure of the energy required to move a molecule of water within the soil matrix. Liquid water 170 resides between solid soil particles 172. In some cases 174, the water substantially completely fills the volume between a group of surrounding soil particles. In other locations, 176, relatively large liquid free regions will be surrounded by liquid filled regions that adhere to soil particles. The liquid regions are themselves bounded by surfaces that generally form a meniscus 178, concave away from the liquid volume 170.

The porous plate 112 has open channels 180 (of which only a few are shown schematically), passing from the specimen surface 126 to the obverse surface 128 of the plate. Ideally, the channels are distributed uniformly throughout the volume of the plate. The liquid adheres to the soil particles, forming meniscus bound droplets at the necks therebetween, and a film around the droplets, in some cases completely surrounding, and in some cases incompletely surrounding. The liquid surrounding the layer of soil particles that contacts the plate 112 is in hydraulic communication with the liquid in the channels 180 within the porous plate 112, which is itself in hydraulic communication with the liquid in the reservoir 130. The reservoir 130 is bounded by the thin elastic wall 132 that bears the strain gauge. The obverse surface 136 of the elastic wall is at or near to atmospheric pressure.

The pore water in the soil specimen is at substantially atmospheric pressure at the beginning of the test, and can be at slightly positive or negative pressure. When the specimen is placed on the porous plate, the hydraulic communication between the liquid in the pore water, and the liquid in the reservoir quickly (within minutes) equilibrates and the entire interconnected volume of liquid assumes the pressure state of the specimen.

As water molecules 182 evaporate from the surfaces of the menisci that are open to atmospheric pressure, the volume of water in the pores diminishes. This volume reduction causes the tension in the menisci to increase, (due to the general tendency to favor smaller surface area to volume ratio) which, in turn results in a greater (absolute value) tension within the interconnected liquid within the specimen pores, the channels 180 in the plate, and the reservoir. A small volume of liquid moves from the reservoir toward the soil specimen, as indicated by the arrows F. Because the obverse face 136 of the elastic wall 132 is exposed to atmospheric pressure, the tension (negative pressure) in the reservoir 130 results in displacement of the elastic wall 132 toward the reservoir 130, and a change in the signal on the strain gauge attached thereto.

One advantage of the present invention, over the prior methods is that the present method directly measures tension which is determined 336 from the displacement of the wall. Therefore any entrapped air in the soil specimen will be accounted for. Any entrapped air in the soil specimen will become larger in volume as the tension (negative pressure) in the pore water increases (in absolute value). In contrast, the prior art pressure plate technique increases the air pressure around the soil specimen and water is then induced to flow out. It is based on an assumption that the pore water will behave the same as if it is under tension (negative pressure), if an equal magnitude, but positive pressure is imposed on the surrounding atmosphere. However, entrapped air will not expand with changes of external air pressure. Therefore, the prior art does not actually mimic the phenomena sought to be examined, (i.e., pore water tension). Therefore, the disclosed method gives results that more accurately reflect the SMC.

Calibration

Figure 5:
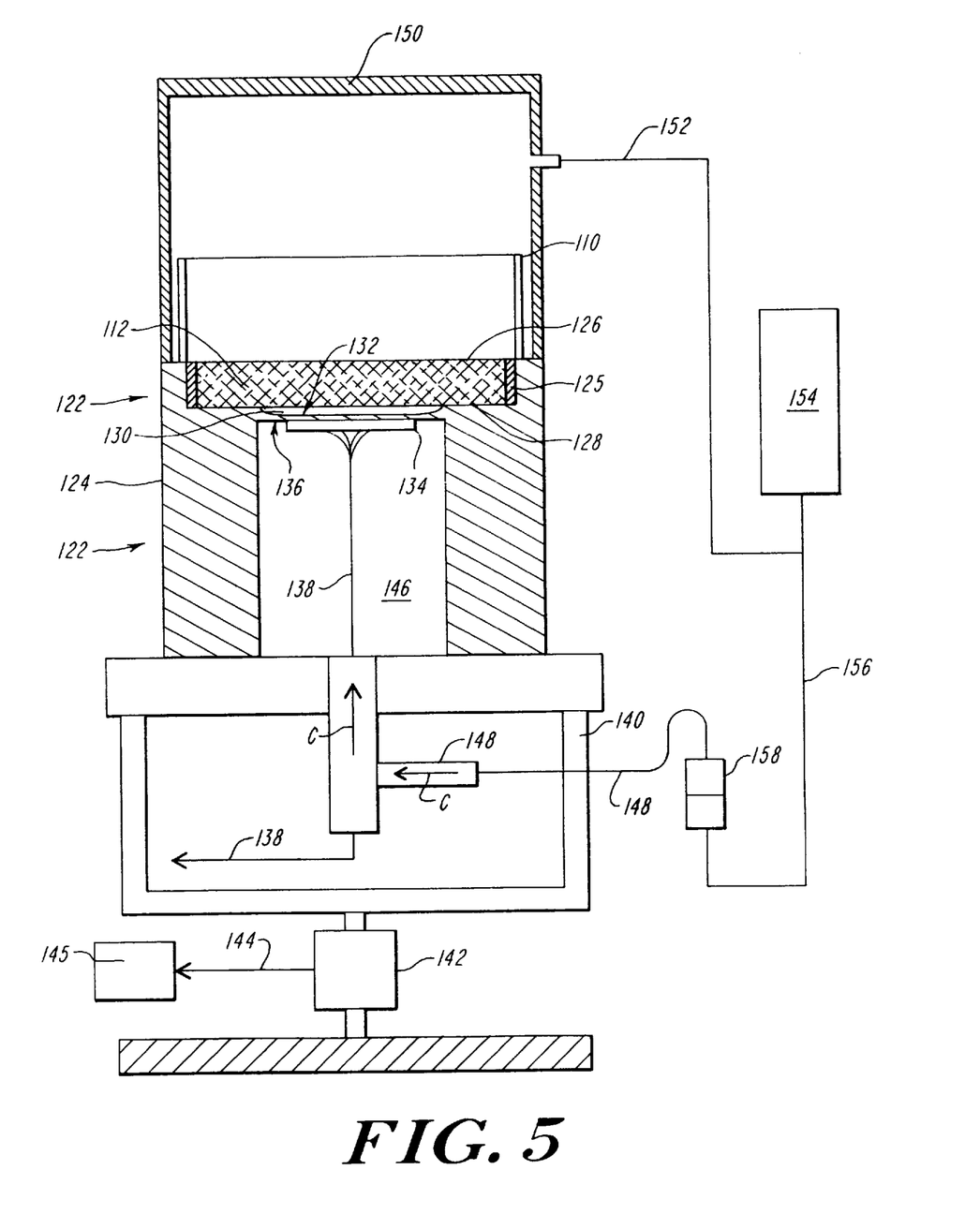
FIG. 5 is a schematic representation of a set up for saturating a porous plate and calibrating a tensiometer used in an apparatus of the invention, such as shown at FIGS. 3 and 4.
Figure 8:
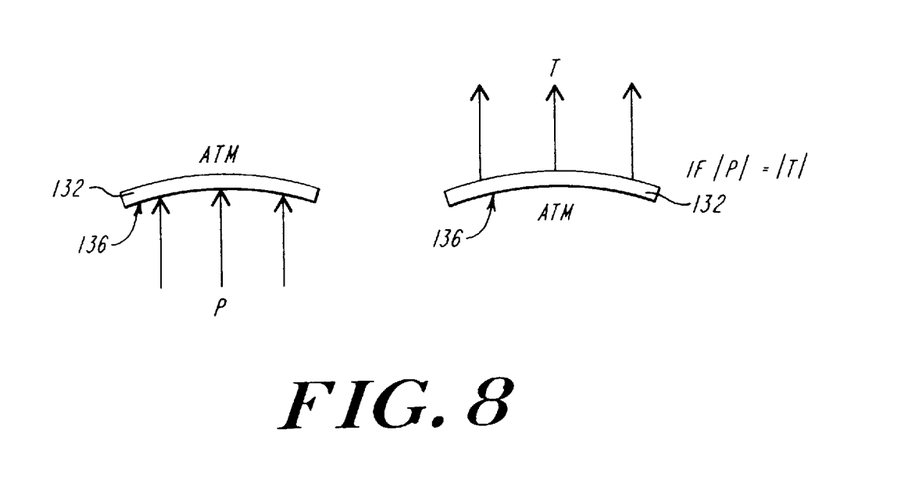
FIG. 8 is a schematic representation of a calibration setup for a preferred embodiment of the invention.

The embodiment described above and shown in FIG. 4 uses a strain gauge 134 as the transducer 121 to measure the water tension. The strain gauge can be calibrated as follows, as shown in FIG. 5. The elastic wall 132 is a wall of the reservoir 130, and also of a second, calibration chamber 146. The elastic wall is thin and acts as a thin diaphragm. As shown in FIG. 8, application of a uniform positive pressure P on the obverse surface 136 of the elastic wall 132 will produce the same deflections (and hence strains) as a uniform tension T (negative pressure) on the reservoir surface of the elastic wall. An applied positive pressure on the obverse surface 136 of the elastic wall is provided by a fluid, such as oil, or gas, such as nitrogen, over a variety of known pressures, into the second chamber 146 through line 148, as indicated by the arrow C. Both the applied pressure and the soil pore water induced tension will be uniform across the elastic wall because the elastic wall is one wall of a fluid filled reservoir. The signal outputs of the strain gauge are read on signal line 138, and recorded in a calibration table against the known pressures. The calibration table may be used as a look-up table during subsequent use of the apparatus, to identify the tension that corresponds to the signal output from the strain gauge 134. Rather than a table, an equation can be fit to the calibration data and can be used to compute tension from the transducer signal.

Saturation

Turning now to saturation of the plate, saturation can be accomplished more efficiently if a vacuum is applied to the plate first, as shown at step 304 in the flow chart of the method, FIG. 9. Saturation is conducted before the specimen is placed on the porous body.

It has been mentioned above that the porous plate 112 must be saturated before it can be used. It has also been mentioned that it must be saturated by applying a pressure of a greater magnitude to the plate 112, and thus the reservoir and the thin elastic wall 132, than the magnitude of the largest tension that will be measured. In fact, it may be required to apply several times the largest tension that will be measured, depending on the properties of the porous plate. It will be understood that, other things being equal, it is desired to keep the elastic wall 132 relatively thin, to increase its sensitivity to changes in tension. On the other hand, if the wall is too thin, then it will not be able to withstand the relatively high pressure required to saturate the porous plate 112. A set-up that can be used to apply a relatively higher saturation pressure using a relatively thinner elastic wall, is shown also with reference to FIG. 5.

A saturation chamber 150 is provided which surrounds the retaining ring 110. It is equally possible to have the saturation chamber enclose the support for the porous body 124 as well. The saturation chamber 150 can be sealed so that water can be introduced through line 152 to fill the chamber 150, in which resides the porous plate 112, adjacent the reservoir 130 and the elastic wall 132. A pressure source 154 provides pressure to the water line 152 and in a preferred embodiment shown in FIG. 5, to a supplementary water line 156, which connects to a water and oil interface 158, which is at equal pressure across the interface, but which keeps the water separate from oil in the line 148. The oil line 148, mentioned above, is connected to the water oil interface, and to the second chamber 146. Thus, the pressure that is provided at the pressure source 154 is delivered to the water that is presented in the saturation chamber 150 to saturate the porous plate 112, and also to the oil in the second chamber 146, which backs up the elastic wall 132, and prevents it from distorting during saturation of the porous plate 112, even if the wall is thinner than would be required to withstand the saturation pressure without any mechanical backing. In a typical case, it is helpful that the saturation backing fluid be electrically non-conducting, to prevent shorting out the strain gauge or other pressure transducer.

It may be helpful to apply the pressure to the second chamber 146 by means of a gas rather than oil. This would require a gas pressure source, which is controlled in such a way as to be equal to the water pressure provided by pressure source 154. This may be accomplished using a completely independent gas pressure source or with the combination of one pressure source plus a water and gas interface.

It should be noted that the thin wall 132 upon which the strain gauge is mounted need not be the bottom wall of the reservoir. Further, the reservoir need not be rectilinear.

Alternative Transducers

Rather than using a strain gauge, other transducers that measure displacement of the elastic membrane 132 can be used, such as a displacement transducer, a proximity sensor, or a pressure transducer. Another preferred embodiment of the invention is shown schematically with reference to FIG. 6. A porous plate 212, substantially identical to the type of plate discussed above, is rigidly fitted within a rigid body 224. Epoxy 215 provides the rigid seal. A rigid seal is important to minimize the occurrence of cavitation, which can arise if the seal is flexible. It might be possible to use o-rings or some other sort of gasket to seal the plate into the support body. However, if o-rings are to be used, care must be taken to avoid the possibility of cavitation at the o-ring. It is believed that o-rings are prone to give rise to cavitation, due to their flexibility and the narrowing gap between the o-ring and the bodies between which it seals. If water does not completely fill this narrowing gap, which it usually does not, then cavitation can arise at the loci of air entrapment as the seal flexes during use. The reason that a rigid seal 215 around the porous body 212 is important also applies to the reason that a rigid seal 125 is used around the porous body 112, and 127 around the generic transducer shown in FIG. 3.

A soil specimen 214 rests on the porous body, retained by a ring 210. A reservoir 230 abuts the face of the porous plate 212, opposite to that upon which the specimen 214 would rest. A pressure transducer 235 is mounted to the body 224 such that its pressure sensitive surface 236 is in hydraulic communication with the reservoir 230, and thus, the porous plate 212. This pressure transducer embodiment and the strain gauge embodiment discussed above are very similar. The major difference is that the reservoir has no elastic membrane wall 132 in this pressure transducer embodiment. The pressure sensitive surface 236 serves the function of the elastic wall 132.

In a typical embodiment, the pressure transducer would also be rigidly sealed into the rigid support body 224, using a layer 260 of a rigid epoxy, or some other suitable, water impervious, rigid barrier. It might be possible to use o-rings, as discussed above, but care must be taken to prevent cavitation. The signal from the pressure transducer is passed by data line 238 to a suitable data acquisition system, as discussed above.

An advantage of using a pressure transducer is that electronic stability and reproducibility are improved, as commercial pressure transducers are very stable, as compared to strain gauge set-ups. The cost of the device would generally be lessened also.

The transducer can be a differential transducer that has a port 237 open to atmospheric pressure in its backside, as shown in dotted line on FIG. 7. This port can be used to calibrate the pressure transducer in the same way as the back-filled oil or gas pressure is used to calibrate a strain gauge set-up, discussed above with reference to FIG. 5. The pressure transducer 235 resides in a second, calibration chamber, just as was discussed above for the strain gauge embodiment. Positive oil or gas pressure is provided to the calibration chamber, and thus to the inside of the pressure transducer, forcing its pressure sensitive surface away from its body, in the same manner as it would be drawn, if under tension applied by the tension in the reservoir.

Non-Soil Applications

The apparatus and method of the invention can also be used to develop MC curves for other porous bodies, such as lumber and concrete, just to name two. A specimen of the item to be studied is placed on a saturated porous plate, just as discussed above, and tested as discussed above. It does not matter that the surface of the specimen is not entirely smooth, because, at the scale of distance that is relevant, a soil specimen is also not smooth. Water, or liquid, collects at the contacts between soil particles or material asperities, forming continuous water or liquid film, and, in many cases, the particles do not contact the porous plate. See FIG. 7.

General Variations

The foregoing discussion should be understood as illustrative and should not be considered to be limiting in any sense. The porous body may be plate-shaped with flat, opposing surfaces, but need not be. It can be any shape that will support the specimen, and provide hydraulic communication to the reservoir. It may be ceramic, or any other suitable porous material. The porous body can also be a composite body with smaller pores towards the surface that is in contact with the soil, as compared to the size of the pores that are nearer to the surface that contacts the reservoir. A thin (e.g., membrane-like) layer may be placed over a ceramic body, such as is described above, to achieve a higher limiting tension. The surface pore size controls the limiting tension.

Various types of tension transducers can be used, such as strain gauges, displacement transducers, pressure gauges, proximity sensors, hall effect sensors, etc. Absolute and differential pressure transducers can be used. To measure mass, a scale, or balance, or force transducer can be used. Rather than graphing the results, they can be presented in tabular form, or simply stored for later use or transmission.

While this invention has been particularly shown and described with references to preferred embodiments thereof, it will be understood by those skilled in the art that various changes in form and details may be made therein without departing from the spirit and scope of the invention as defined by the claims.

The corresponding structures, materials, acts and equivalents of all means or step plus function elements in the claims below are intended to include any structure, material, or acts for performing the functions in combination with other claimed elements as specifically claimed.

Having described the invention, what is claimed is:

1. A method for generating a signal that corresponds to a moisture content characteristic, which characteristic relates tension in liquid residing within a specimen of a porous material, to liquid content of the specimen, the method comprising the steps of:
   a. providing apparatus comprising:
      i. a porous body having a specimen surface and a reservoir surface, the reservoir surface facing and in hydraulic contact with a reservoir;
      ii. a first transducer, coupled to the reservoir and arranged upon activation to generate a signal that corresponds to tension within the reservoir; and
      iii. supporting the porous body, a second transducer, arranged upon activation to generate a signal that corresponds to the mass of the specimen;
   b. saturating the pores of the porous body and filling the reservoir with the liquid;
   c. placing the specimen upon the specimen surface of the porous body, in hydraulic contact with the porous body;
   d. monitoring a signal from the first transducer, and correlating the signal to tension within the reservoir;
   e. while conducting the step of monitoring the signal from the first transducer, the step of causing the liquid to exit the specimen; and
   f. while conducting the steps of monitoring the signal from the first transducer, and causing liquid to exit the specimen, further conducting the steps of:
      i. monitoring a signal from the second transducer; and
      ii. correlating the signal from the second transducer to liquid content of the sample, to arrive at the moisture content characteristic.

2. The method of claim 1, the first transducer comprising a pressure transducer, the pressure transducer having a pressure sensitive member that is in hydraulic communication with the reservoir.

3. The method of claim 1, the reservoir being partially bound by an elastic wall, the first transducer comprising a strain gauge that is coupled to the elastic wall to generate a signal that corresponds to strain of the wall.

4. The method of claim 1, the steps of monitoring the signals from the first and second transducers comprising the step of periodically recording the signals and correlating the signals with the time at which they were recorded.

5. The method of claim 1, the second transducer comprising a balance.

6. The method of claim 1, the second transducer comprising a force transducer.

7. The method of claim 1, the step of causing the liquid to exit the specimen comprising the step of allowing the liquid to evaporate from the specimen.

8. The method of claim 1, further comprising the step of providing a desiccant material near to the specimen, to promote the exit of liquid from the specimen.

9. The method of claim 4, further comprising the step of correlating the signal that corresponds to mass of the specimen at a specific time to the signal that corresponds to tension in the specimen at the same specific time.

10. The method of claim 9, the step of correlating the mass signal and the tension signal to each other comprising the step of correlating the mass signal and the tension signal at a plurality of times.

11. The method of claim 10, the step of correlating the mass signal and the tension signal at a plurality of times comprising correlating the signals graphically.

12. The method of claim 10, the step of correlating the mass signal and the tension signal at a plurality of times comprising correlating the signals tabularly.

13. The method of claim 1, the specimen comprising soil.

14. The method of claim 1, the specimen comprising wood.

15. The method of claim 1, the specimen comprising concrete.

16. The method of claim 3, the step of saturating the porous body comprising the steps of simultaneously applying liquid under pressure to the specimen surface of the porous body and liquid under opposite and substantially equal magnitude pressure to the elastic wall, opposite the reservoir.

17. The method of claim 3, the step of saturating the porous body comprising the steps of simultaneously applying liquid under pressure to the specimen surface of the porous body and gas under opposite and substantially equal magnitude pressure to the elastic wall, opposite the reservoir.

18. The method of claim 16, further comprising, before the saturating step, the step of applying a vacuum to the porous body.

19. The method of claim 1, further comprising, before the step of placing the specimen, the step of calibrating the first transducer by the steps of:
   a. applying a plurality of known, positive pressures to the elastic wall, opposite the reservoir;

b. collecting a signal output from the first transducer corresponding to each of the plurality of positive pressures; and c. recording the signals against the known positive pressures, thereby calibrating the first transducer.

20. The method of claim 1, the step of correlating the signal from the second transducer comprising the steps of:

a. removing the specimen from the body;

b. measuring the mass of the specimen;

c. drying the specimen, to remove substantially all of the liquid; and d. measuring the mass of the dried specimen.

21. An apparatus for generating a signal that corresponds to a moisture content characteristic, which characteristic relates tension in liquid residing within pores of a specimen of a porous material, to liquid content of the specimen, the apparatus comprising:

a. a porous body, having a specimen surface and a reservoir surface;

b. a reservoir, adjacent the reservoir surface of the porous body, the porous body arranged with the reservoir surface in hydraulic communication with the reservoir;

c. a first transducer, coupled to the reservoir and arranged, upon activation, to generate a signal that corresponds to tension within the reservoir; and d. supporting the porous body, a second transducer, arranged, upon activation, to generate a signal that corresponds to mass of the specimen.

22. The apparatus of claim 21, the first transducer comprising a pressure transducer, having a pressure sensitive member that is in hydraulic communication with the reservoir.

23. The apparatus of claim 21, further comprising a rigid seal that seals the porous body from an atmosphere surrounding the apparatus on all surfaces except the specimen surface and the reservoir surface.

24. The apparatus of claim 21, further comprising a rigid seal that seals the reservoir from an atmosphere surrounding the apparatus, except at the reservoir surface of the porous body.

25. The apparatus of claim 21, the reservoir being partially bound by an elastic wall having a reservoir face facing the reservoir, and an obverse face, the first transducer comprising a strain gauge that is coupled to the elastic wall, arranged upon activation to generate a signal that corresponds to strain of the wall.

26. The apparatus of claim 21, the reservoir being partially bound by an elastic wall having a reservoir face facing the reservoir, and an obverse face, the first transducer comprising a displacement transducer, arranged upon activation to generate a signal that corresponds that to displacement of the elastic wall.

27. The apparatus of claim 21, further comprising means for correlating the signal that corresponds to tension to a time at which the tension signal was generated.

28. The apparatus of claim 21, further comprising means for correlating the signal that corresponds to mass to a time at which the mass signal was generated.

29. The apparatus of claim 27, further comprising means for correlating the signal that corresponds to mass to a time at which the signal was generated, and for correlating a mass signal and a tension signal that both correspond to an identical time, to each other.

30. The apparatus of claim 29, the means for correlating the mass and tension signals that correspond to an identical time comprising means for graphing the mass and tension signals relative to each other.

31. The apparatus of claim 25, the second transducer comprising a force sensor.

32. The apparatus of claim 25, the second transducer comprising a balance.

33. The apparatus of claim 21, the porous body comprising, pores having a pore diameter of between 50 and 30 nm, with a pore volume of between 0.1 and 0.8 $cm^3/g$.

34. The apparatus of claim 21, the porous body being characterized by a measuring tension having an upper limit and a saturation pressure having a greater absolute value of an upper limit, the elastic wall being capable of withstanding a pressure differential having an absolute value greater to or equal to the measuring tension upper limit absolute value, but less than the saturation pressure upper limit absolute value.

35. The apparatus of claim 21, further comprising a second, pressurizeable chamber that includes as a wall, the obverse face of the elastic wall.

36. The apparatus of claim 35, further comprising means for providing liquid at a positive pressure relative to atmospheric to the porous body, and thereby to the reservoir face of the elastic wall.

37. The apparatus of claim 36, further comprising means for providing fluid at a positive pressure relative to atmospheric to the second, pressurizeable chamber.

38. The apparatus of claim 36, further comprising means for providing gas at a positive pressure relative to atmospheric to the second, pressurizeable chamber.

39. The apparatus of claim 37, further comprising means for simultaneously providing fluid at a positive pressure to the porous body and to the second, pressurizeable chamber.

40. The apparatus of claim 22, the pressure transducer comprising a differential pressure transducer.

41. The apparatus of claim 22, the porous body comprising a ceramic.

42. The apparatus of claim 22, the porous body comprising a plate shape, with opposing substantially flat, parallel surfaces.

43. The apparatus of claim 21, further comprising means for causing liquid to evaporate from the specimen.

* * * * *